(12) United States Patent
Tets et al.

(10) Patent No.: US 10,307,424 B2
(45) Date of Patent: Jun. 4, 2019

(54) DRUG WITH HEPATOPROTECTIVE ACTIVITY

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Konstantin Andreevich Krasnov, St. Petersburg (RU)

(73) Assignees: Georgy Viktorovich Tets, Saint-Petersburg (RU); Viktor Veniaminovich Tets, Saint-Petersburg (RU)

( * ) Notice: Subject to any disclaimer, the term of this patent is extended or adjusted under 35 U.S.C. 154(b) by 52 days.

(21) Appl. No.: 15/562,294

(22) PCT Filed: Mar. 23, 2016

(86) PCT No.: PCT/RU2016/000160
§ 371 (c)(1),
(2) Date: Sep. 27, 2017

(87) PCT Pub. No.: WO2016/159833
PCT Pub. Date: Oct. 6, 2016

(65) Prior Publication Data
US 2018/0338975 A1 Nov. 29, 2018

(30) Foreign Application Priority Data
Mar. 27, 2015 (RU) .................. 2015111184

(51) Int. Cl.
*A61K 31/513* (2006.01)
*A61P 1/16* (2006.01)
*A61K 45/06* (2006.01)
*C07D 239/545* (2006.01)

(52) U.S. Cl.
CPC ............ *A61K 31/513* (2013.01); *A61K 45/06* (2013.01); *A61P 1/16* (2018.01); *C07D 239/545* (2013.01)

(58) Field of Classification Search
CPC .............. C07D 239/545; C07D 239/60; C07D 239/62; C07D 239/64
See application file for complete search history.

(56) References Cited

U.S. PATENT DOCUMENTS 4,254,103 A 3/1981 Timar
6,624,202 B2 9/2003 Smith et al.
(Continued)

FOREIGN PATENT DOCUMENTS

EP 1083172 A1 3/2001
EP 1986651 B1 10/2011
(Continued)

OTHER PUBLICATIONS

H.C. Kim et al., BMJ (2000) (Year: 2000).*
M. Kew, The Lancet (2000) (Year: 2000).*
March, J., "Advanced Organic Chemistry: Reactions, Mechanisms, and Structure", Fourth Edition, Copyright (1992), pp. 72-73.
Pankratov A. N. Kisloty i osnovaniya v khimii: Ushebnoe posobie v kontekste nauchnogo napravleniya, 2009, Saratov, 32 p, especially p. 25. (English Translation).
(Continued)

*Primary Examiner* — Alexander R Pagano
(74) *Attorney, Agent, or Firm* — Troutman Sanders LLP

(57) ABSTRACT

The invention relates to pharmacology and can be used for treating liver diseases of various etiologies, inter alia, in combination with other preparations. Claimed is a drug with hepatoprotective activity comprised of 3-(4-bromophenyl)-6,6-dihydroxy-5-hydroxyiminohexahydro-2,4-pyrimidinedione and salts thereof of general formula (I),

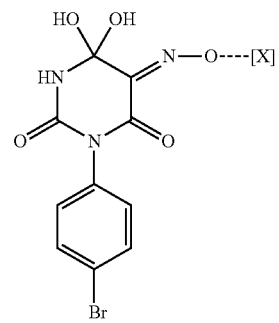

where X is selected from the group: H, Na, K, or from the group of hydroxyalkylammonia derivatives of general formula (II),

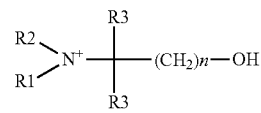

where R1, R2 are selected from the group: H, $CH_3$, $CH_2CH_3$, $CH_2CH_2OH$;
R3 is selected from the group: H, $CH_2OH$; and n=1, 2;
the drug can be prepared in the form of tablets or capsules for enteral administration; or in the form of a liquid or lyophilized substance for parenteral administration; or in the form of rectal suppositories; or in the form of capsules or tablets, or sweets for sucking; and may additionally contain the hepatoprotector Heptral; or the hepatoprotector Essentiale; or the hepatoprotector ursodeoxycholic acid. This increases the effectiveness of a drug with hepatoprotective activity.

24 Claims, No Drawings

(56) References Cited

U.S. PATENT DOCUMENTS

| | | | |
|---|---|---|---|
| 7,074,925 B1* | 7/2006 | Ashkinazi | C07D 239/60 544/299 |
| 7,851,479 B2 | 12/2010 | Kwon et al. | |
| 8,962,640 B2 | 2/2015 | Tets et al. | |
| 8,999,959 B2 | 4/2015 | Tets et al. | |
| 9,730,933 B2 | 8/2017 | Tets et al. | |
| 2002/0173521 A1 | 11/2002 | Smith et al. | |
| 2004/0106654 A1 | 6/2004 | Smith et al. | |
| 2009/0023764 A1 | 1/2009 | Kwon et al. | |
| 2012/0157483 A1 | 6/2012 | Tets et al. | |
| 2013/0237704 A1 | 9/2013 | Tets et al. | |
| 2015/0158825 A1 | 6/2015 | Tets et al. | |
| 2016/0250214 A1 | 9/2016 | Tets et al. | |

FOREIGN PATENT DOCUMENTS

| | | |
|---|---|---|
| EP | 2638900 A1 | 9/2013 |
| JP | 2008074807 A | 4/2008 |
| RU | 2188196 C2 | 8/2002 |
| RU | 2003103291 A | 1/2005 |
| RU | 2400233 C1 | 9/2010 |
| WO | 1999061427 A1 | 12/1999 |
| WO | 2011005142 A1 | 1/2011 |

OTHER PUBLICATIONS

J.A. Bonacin, et al., "Vibrational spectra and theoretical studies of tautomerism and hydrogen bonding in the violuric acid and 6-amino-5nitrosouracil system", Vibrational Spectroscopy (2007), vol. 44, No. 1, pp. 133-141.
European Search Report dated Feb. 27, 2014, from corresponding European Application No. EP11839641.5, 6 pages.
E.E. Frezza, et al., "Sex Hormones and trace elements in rat CCL4-induced cirrhosis and hepatocellular carcinoma", European Journal of Cancer Prevention (1993), vol. 2, pp. 357-359.
Gornostaev L. M., "Tautomeriya organicheskikh soedinenii" (The Tautomerism in Organic Chemistry), Sorosovkii Orbazovatelnyi zhurnal (Soros Educational Journal), (1996), No. 4, pp. 33-38.
Translation of International Preliminary Report on Patentability dated May 14, 2013, from corresponding International Application No. PCT/RU2011/000792.
Translation of International Search Report dated Feb. 2, 2012, from corresponding International Application No. PCT/RU2011/000792.
Translation of the Written Opinion of the International Searching Authority dated Jan. 26, 2012, from corresponding International Application No. PCT/RU2011/000792.
Communication Pursuant to Article 94(3) EPC issued in European Patent Application No. 11839641.5, dated Jul. 10, 2017, 6 pages.
International Search Report Issued in International Application No. PCT/RU2016/000160, dated Sep. 1, 2016 and English Translation Thereof, 5 pages.
Dzh. March. Organic Chemistry. Reactions, mechanisms, and structure. Advanced course for universities and chemical colleges. M., Mir, 1987, v.3, p. 325-327 and English Translation.
Technology of medicinal forms, edited by T.S. Kondradevoi. M. Meditsina. 1991, v.1, p. 10-11 and English Translation.
Kucheriavyi lu.A. et al. Hepatoprotectors: rational applications. Tutorial for doctors, M., Forte Print, 2012, p. 29, 32 and English Translation.
Wikipedia, "S-Adenosyl methionine", https://en.wikipedia.org/wiki/S-Adenosyl_methionine, 5 pages.
J. March. Advanced Organic Chemistry. Reactions, mechanisms, and structure. Advanced course for universities and chemical colleges. M., Mir, 1987, v.3, p. 325-327 and English Translation.
Technology of medicinal forms, edited by T.S. Kondratyevai. M. Meditsina. 1991, v.1, p. 10-11 and English Translation.
Kucheriavyi lu.A. et al. Hepatoprotectors: rational aspects of application. Educational Handbook for physicians, M., Forte Print, 2012, p. 29, 32 and English Translation.

* cited by examiner

DRUG WITH HEPATOPROTECTIVE ACTIVITY

CROSS-REFERENCE TO RELATED APPLICATIONS

This application is a U.S. National Phase of International Patent Application No. PCT/RU2016/000160, filed on Mar. 23, 2016, which published as WO 2016/159833 A1 on Oct. 6, 2016, and claims priority to Russian Patent Application No. 2015111184, filed on Mar. 27, 2015, all of which are herein incorporated by reference in their entirety.

TECHNICAL FIELD

The invention relates to pharmacology and can be used for treating liver diseases of various etiologies, inter alia, in combination with other preparations.

BACKGROUND ART

There is a commonly known hepatoprotective solution which is a complex of peptides obtained by extraction from the liver of cattle, U.S. Pat. No. 4,254,103 A, publ. Mar. 3, 1981.

Also known is a hepatoprotector with antioxidant activity, containing natural substances, namely, walnut core shell or its extract JP 2008074807 (A), publ. Mar. 4, 2008.

The drawbacks of the above extracts of animal and vegetable origin are:

impossibility to control the composition and quality of extracts;

frequent allergic reactions;

low efficiency.

The use of a substance representing a derivative of methionine and adenosine triphosphate (S-Adenosyl methionine-ademetionine), as a pharmaceutical for the treatment of various liver diseases.

This drug is taken as a prototype of the subject drug with hepatoprotective activity.

The drug is indicated for treatment of chronic hepatitis, intrahepatic cholestasis, liver cirrhosis, hepatic encephalopathy, withdrawal syndrome, etc. Ademetionin is present in all living cells and plays the key role in important biochemical reactions (transmethylation, transsulfation, synthesis of polyamines), however, natural ademetionine is unstable. Stable synthetic ademetionine was obtained in 1974 in Italy, but its therapeutic effectiveness cannot be considered sufficient.

SUMMARY OF THE INVENTION

It is an object of the present invention to improve the efficacy of the drug with hepatoprotective activity.

According to the invention, the objective of the invention is achieved by providing a drug with hepatoprotective activity that is 3-(4-bromophenyl)-6,6-dihydroxy-5-hydroxyiminohexahydro-2,4-pyrimidinedione and its salts of the following general formula:

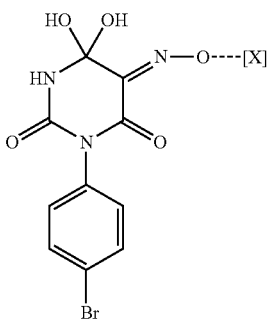

wherein X is selected from the following group: H, Na, K, or from the group of derivatives of hydroxyalkyl ammonia of the general formula

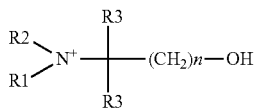

wherein R1 and R2 are selected from the following group: H, $CH_3$, $CH_2CH_3$, $CH_2CH_2OH$;

R3 is selected from the following group: H, $CH_2OH$; n=1, 2; the drug can be prepared in the form of tablets or capsules for enteral administration; or in the form of a liquid or lyophilized substance for parenteral administration; or in the form of rectal suppositories; or in the form of capsules or tablets, or sweets for sucking; and may additionally contain the hepatoprotector Heptral; or the hepatoprotector Essentiale; or the hepatoprotector ursodeoxycholic acid.

The invention includes all spatial isomers of the subject compounds and all of their tautomeric forms.

The applicant is not aware of any sources of information that would contain information about identical technical solutions, which makes it possible to conclude that the claimed invention complies with the "Novelty" ("N") criterion.

Due to the implementation of the subject technical solution, a technical result is achieved, consisting in a significant increase in the effectiveness of the drug.

The applicant has not found any sources of information containing data on the effect of the distinctive features of the invention on the technical result achieved due to their implementation. This, according to the applicant, demonstrates the compliance of this technical solution with the condition of patentability "Inventive Step" ("IS").

BRIEF DESCRIPTION OF THE DRAWINGS

In the following, the invention is explained with a detailed description of examples of its implementation without reference to the drawings.

PREFERRED EMBODIMENT

To solve the problem, the derivatives listed in Table 1 are preferred.

Derivative 1 of the subject substance is synthesized in 4 stages in accordance with Diagram 1, and derivatives 2-9, which are salts of derivative 1, are obtained by exposing derivative 1 to the corresponding bases according to Diagram 2.

Diagram 1.

Synthesis of 3-(4-bromophenyl)-6,6-dihydroxy-5-hydroxyiminohexahydro-2,4-pyrimidinedione (derivative 1)

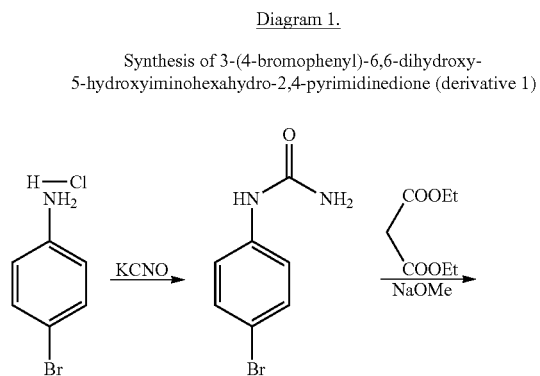

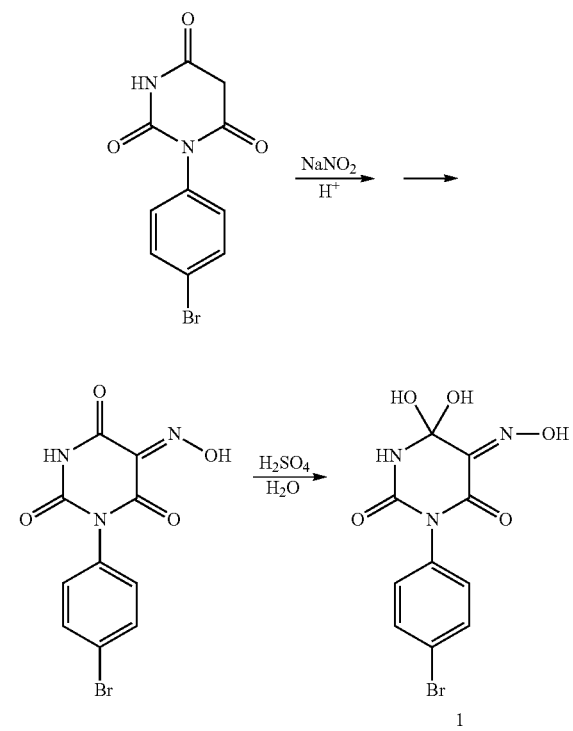

Diagram 2. Synthesis of derivatives 2-9

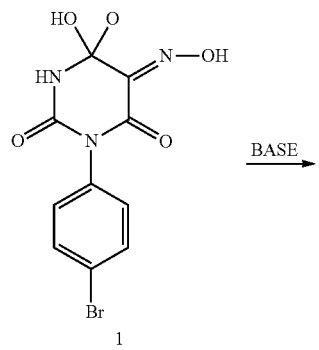

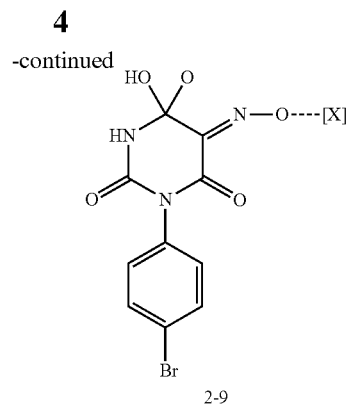

2-9

Table 2 shows the decoding of the reagents (bases) used to synthesize derivatives 2-9.

Example 1. Preparation of 3-(4-bromophenyl)-6,6-dihydroxy-5-hydroxyiminohexahydro-2,4-pyrimidinedione (Derivative 1)

In the first step, 1 mole (172 g) of p-bromoaniline is dissolved while heating to 50° C. in 2.5 l of water and adding 1.1 moles of HCl (105 ml of 30% hydrochloric acid). 1.1 mol (81 g) of potassium cyanate dissolved in 400 ml of water is added to the solution while stirring. The obtained mixture is heated for 15 min in a water bath, then cooled, a white crystalline precipitate is separated and flushed with water and then with aqueous alcohol, after which the precipitate is air dried to constant weight at 50° C. As a result, 175 g of N-(4-bromophenyl)urea in the form of a colorless crystalline solid is obtained. The yield is 81% of the theoretical value.

In the second step, 2 moles (46 g) of metallic sodium are dissolved in 600 ml of anhydrous methanol. 1 mole (160 g) of diethyl malonic ether is added to the obtained solution and stirred for 5 minutes. Then 1 mole (215 g) of N-(4-bromophenyl)urea is added and the mixture is boiled for 6 hours under reflux while stirring. Then the mixture is cooled to 25° C. and 2 L of water is added. The solution is filtered from the precipitate, after which the filtrate is acidified with HCl to pH 1, after which the formed precipitate is filtered and flushed with water. The resulting raw product is treated while stirring with 2 liters of water added to 100 ml of 25% aqueous ammonia, the insoluble residue is discarded, and the solution is acidified with HCl to pH 1, the formed residue is filtered, flushed with water and dried. 250 g of 1-(4-bromophenyl)barbituric acid are obtained in the form of a colorless crystalline product with the melting point of 261-263° C. The yield is 89% of the theoretical value.

In the third step, 1 mole (283 g) of 1-(4-bromophenyl) barbituric acid is dissolved in 3 L of water containing 1 mole (40 g) of NaOH. Into the resulting clear solution a solution of 75 g (1.1 mol) of sodium nitrite in 400 ml of water is poured and then stirred. The solution is cooled to 10° C., then while stirring, 1.2 mol (72 g) of acetic acid is added dropwise and kept at 25° C. for 1 hr. Then 200 ml of 30% hydrochloric acid are added to the obtained mixture and stirred for 10 minutes. The formed precipitate is filtered and flushed with 1% solution of HCl, then with water, and dried. 284 g of 1-(4-bromophenyl)violuric acid in the form of a pale yellow crystalline product with the melting point of 220° C. (with decomp.) is obtained. The yield is 91% of the theoretical value.

In the fourth step, 50 ml of 90% sulfuric acid are added to 9.36 g (0.03 mol) of 1-(4-bromophenyl)violuric acid and stirred at room temperature until dissolved. The resulting solution is added dropwise with vigorous stirring to 300 ml of ice water containing 200 g of crushed ice, ensuring that the temperature of the mixture does not exceed 3° C. The formed residue is separated on a glass filter, flushed with cold water until a neutral flush reaction occurs, and dried in air at room temperature to obtain 7.10 g of the desired product 3-(4-bromophenyl)-6,6-dihydroxy-5-hydroxyiminohexahydro-2,4-pyrimidinedione (1) in the form of a substantially colorless, fine crystalline powder.

The yield and the melting point of the obtained substance (1) are given in Table 3, the VUR spectrum data are given in Table 4, the elemental analysis data are given in Table 5.

Example 2. Synthesis of Derivatives (2-4)

300 ml of water containing an equimolar amount of the appropriate base (NaOH, KOH or tris-hydroxymethylaminomethane, see table 2) are poured into 16.50 g (0.05 mol) of 3-(4-bromophenyl)-6,6-dihydroxy-5-hydroxyiminohexahydro-2,4-pyrimidinedione (1). The mixture is heated to a temperature of no higher than 60° C. and stirred for 10 minutes, after which the solution is filtered, poured into vials for freeze drying and frozen at −20° C. After lyophilization, the desired product (2-4) is obtained in the form of a colored porous mass.

Example 3. Synthesis of Derivatives (5-9)

60 ml of water are added to 16.50 g (0.05 mol) of 3-(4-bromophenyl)-6,6-dihydroxy-5-hydroxyiminohexahydro-2,4-pyrimidinedione (1) and an equimolar amount of the corresponding base (1-aminopropan-3-ol, dimethylaminoethane-2-ol, diethylaminoetan-2-ol, N,N-diethanolamine or N-triethanolamine) (15-20) (see Table 2). The mixture is heated to a temperature of no higher than 60° C. and stirred for 10 minutes, with incomplete dissolution, another 10 ml of water are added and mixed for 5 minutes until complete dissolution.

The solution is filtered and then the solvent is removed in vacuo on a rotary evaporator at a temperature of no higher than 30° C. The residue is washed with 30 ml of alcohol, the precipitate is filtered off and air dried at room temperature to obtain the derivatives (5-9) in the form of a colored crystalline powder.

The yield and the melting point of the obtained derivatives (1-9) are given in Table 3, the VUR spectrum data are given in Table 4, the elemental analysis data are given in Table 5.

Example 4

A study of hepatoprotective activity of derivatives 1-9 was performed on Wistar rats of both sexes weighing 195-245 grams. The animals were in standard housing conditions under natural light conditions, with free access to water and food. Acute toxic hepatitis in rats was induced by means of intragastric administration of 50% solution of carbon tetrachloride (CCl 4) in olive oil at a dose of 1 ml/kg for 6 days. After 10 days all experimental animals confirmed the presence of toxic hepatitis according to the morphological pattern of the liver. The total duration of the experiment was 20 days.

The tested preparations were administered orally in the form of a suspension in olive oil once a day after the formation of the model pathology or intravenously at a dose of 25 mg/kg. The weight dynamics of the rats were determined on Sartorius scale.

The results are given in Tables 6 and 7.

The study of the efficacy of derivatives No. 1 and No. 2 was additionally carried out with the participation of patients (men and women aged 25 to 60 years) with the following diagnoses: toxic liver damage, alcoholic hepatitis, alcoholic liver disease (fatty hepatosis), alcoholic liver cirrhosis.

Inclusion criteria: increased levels of alanine aminotransferase (ALT), aspartate aminotransferase (ASAT), gamma glutaminetransferase (GGTP) at least 2 times the upper limit of the normal value.

Derivative No. 1

Patients of the experimental group (30 persons) adhibited derivative No. 1 in the form of capsules containing 250 mg of the drug in a total dose of 1000 mg/day.

Patients of the control group (9 persons) adhibited placebo (capsules filled with chalk).

The dynamics of the decrease in ALT is presented in Table 8.

The dynamics of the decrease in ASAT is presented in Table 9.

The dynamics of the decrease in gamma glutaminetransferase is presented in Table 10.

Derivative No. 2

Patients of the experimental group (30 persons) adhibited derivative No. 2 in the form of lyophilisate for IV injection containing 50 mg of the drug in a total dose of 300 mg/day.

Patients of the control group (10 persons), were administered a 0.9% solution of NaCl as a placebo.

The dynamics of the decrease in ALT is presented in Table 11.

The dynamics of the decrease in ASAT is presented in Table 12.

The dynamics of the decrease in gamma glutaminetransferase is presented in Table 13.

The efficacy of derivative No. 4 on additional parameters was studied in laboratory rats.

For the modeling of toxic hepatitis, the combined administration of dichloroethane and acetaminophen in doses of 300 and 250 mg/kg, respectively, was used. After 10 days all experimental animals confirmed the presence of toxic hepatitis according to the morphological pattern of the liver. In the untreated control group, by the 10th day of the study, 4 animals out of 10 died. In groups where animals were enterally or parenterally injected with derivative No. 4, not a single animal died.

From that time, for 10 days, the experimental animals were administered, once a day, derivative No. 4 (50 mg/kg, intragastrically in starch mucus) or derivative No. 4 (10 mg/kg, IV, into the tail vein).

Also, the combined effect of the subject compounds and known drugs for the treatment of hepatic diseases was examined.

For the modeling of toxic hepatitis, the combined administration of dichloroethane and acetaminophen in doses of 500 and 500 mg/kg, respectively, was used. After 10 days all experimental animals confirmed the presence of toxic hepatitis according to the morphological pattern of the liver.

The results of the study are presented in Table 17.

INDUSTRIAL APPLICABILITY

The invention is implemented using common materials and equipment, resulting, according to the applicant's opinion, in compliance of the invention with the "Industrial Applicability" ("IA") patentability criterion.

Table 1

The structure of the most active of the subject derivatives (1-9) of the general formula

TABLE 2

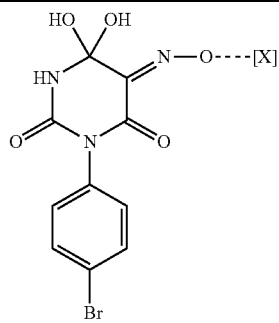

| No. | X | R1 | R2 | R3 | n |
|---|---|---|---|---|---|
| 1 | H | — | — | — | — |
| 2 | Na | — | — | — | — |
| 3 | K | — | — | — | — |
| 4 | R2\N+—(CH₂)n—OH / R1 R3 | H | H | CH₂OH | 1 |
| 5 | | H | H | H | 2 |
| 6 | | CH₃ | CH₃ | H | 1 |
| 7 | | CH₂CH₃ | CH₂CH₃ | H | 1 |
| 8 | | CH₂CH₂OH | H | H | 1 |
| 9 | | CH₂CH₂OH | CH₂CH₂OH | H | 1 |

The structure of the bases used to obtain derivatives (2-9)

TABLE 3

| Reference base | The synthesized subject substance, No. |
|---|---|
| NaOH | 2 |
| KOH | 3 |
| H₂N—C(CH₂OH)₃ | 4 |
| H₂N—CH₂CH₂CH₂OH | 5 |
| (CH₃)₂N—CH₂CH₂OH | 6 |
| Et₂N—CH₂CH₂OH | 7 |
| HN(CH₂CH₂OH)₂ | 8 |
| N(CH₂CH₂OH)₃ | 9 |

The yield and the melting point of derivatives 1-9

TABLE 4

| Substance No. | Yield, % | Melting point (dec) |
|---|---|---|
| 1 | 74 | 220-222 |
| 2 | 99 | >290 |
| 3 | 99 | >290 |
| 4 | 99 | 199-201 |
| 5 | 96 | 205-207 |
| 6 | 91 | 216-219 |
| 7 | 89 | 213-215 |
| 8 | 90 | 222-225 |
| 9 | 86 | 225-227 |

$^1$H NMR spectra data for derivatives 1-9 in DMSO-$d_6$

TABLE 5

| | Chemical shift, ppm, J, Hz | | | | |
|---|---|---|---|---|---|
| Substance No. | ArH, 2H + 2H, d + d or d.d, J 8.0 | NH, br. s, (1H) | OCH₂ | NCH₂ (NCH) | Other H |
| 1 | 2 | 3 | 4 | 5 | 6 |
| 1 | 7.22 + 7.27 (d + d, 2H), 7.68 (d.d, 2H) | 11.77 | — | — | 1.76 br. s, (1H, NOH). |
| 2 | 7.15 (d, 2H), 7.64 (d, 2H) | 11.18 | — | — | — |
| 3 | 7.15 (d, 2H), 7.64 (d, 2H) | 11.18 | — | — | — |
| 4 | 7.09 + 7.51, d + d | 11.13 | 3.49 s (6H) | — | 5.25 br. s (3H, OH), 7.01 br. s (3H, NH₃⁺) |
| 5 | 7.09 + 7.51, d + d | 11.18 | 3.52 t (2H) | 2.99 $_T$(2H) | 1.72 m (2H, CH₂), 6.80 br. s (3H, NH₃⁺) |
| 6 | 7.12 + 7.55, d + d | 11.07 | 3.72 t (2H) | 3.22 t (2H) | 2.67 s (6H, 2NMe₂) |
| 7 | 7.15 + 7.56, d + d | 11.10 | 3.74 t (2H) | 3.23 m (6H) | 1.02 (t, 6H) |
| 8 | 7.10 + 7.52, d + d | 11.15 | 3.70 t (4H) | 3.19 t (4H) | 7.24 br. s (2H, NH₂⁺) |
| 9 | 7.13 + 7.54, d + d | 11.09 | 3.77 t (6H) | 3.24 t (6H) | — |

Elemental analysis of derivatives 1-9

TABLE 6

| Substance No. | Found, % C | Found, % H | Found, % N | Gross formula | Calculated, % C | Calculated, % H | Calculated, % N |
|---|---|---|---|---|---|---|---|
| 1 | 36.46 | 2.33 | 12.82 | $C_{10}H_8BrN_3O_5$ | 36.39 | 2.44 | 12.73 |
| 2 | 34.22 | 1.89 | 11.99 | $C_{10}H_7BrNaN_3O_5$ | 34.12 | 2.00 | 11.93 |
| 3 | 32.62 | 1.80 | 11.41 | $C_{10}H_7BrKN_3O_5$ | 32.62 | 1.92 | 11.41 |
| 4 | 37.41 | 4.12 | 12.53 | $C_{14}H_{19}BrN_4O_8$ | 37.27 | 4.24 | 12.42 |
| 5 | 38.71 | 4.06 | 14.01 | $C_{13}H_{17}BrN_4O_6$ | 38.53 | 4.23 | 13.83 |
| 6 | 40.32 | 4.29 | 13.55 | $C_{14}H_{19}BrN_4O_6$ | 40.11 | 4.57 | 13.36 |
| 7 | 43.05 | 5.07 | 12.60 | $C_{16}H_{23}BrN_4O_6$ | 42.97 | 5.18 | 12.53 |
| 8 | 38.69 | 4.30 | 12.93 | $C_{14}H_{19}BrN_4O_7$ | 38.64 | 4.40 | 12.87 |
| 9 | 40.14 | 4.80 | 11.72 | $C_{16}H_{23}BrN_4O_7$ | 40.10 | 4.84 | 11.69 |

Survivability of the animals

TABLE 7

| | Survivability of the animals by day 28 (in %) | |
|---|---|---|
| | Intraventricular administration | Intravenous administration |
| Control 1— not treated with $CCl_4$ | 100 | 100 |
| Control 2 — treated with $CCl_4$, not treated with drugs | 5 | 5 |
| Prototype | 46 | 48 |
| 1 | 59 | 57 |
| 2 | 57 | 58 |
| 3 | 59 | 60 |
| 4 | 58 | 56 |
| 5 | 61 | 60 |
| 6 | 55 | 59 |
| 7 | 57 | 60 |
| 8 | 59 | 59 |
| 9 | 58 | 60 |

Body weight of the surviving animals

TABLE 8

| | Body weight of the animals by the 20th day (in %) | |
|---|---|---|
| | Intraventricular administration | Intravenous administration |
| Control 1— treated with $CCl_4$ | 175 ± 6 | 175 ± 6 |
| Control 2— treated with CCl4, not treated with drugs | 137 ± 9 | 137 ± 9 |
| Prototype | 160 ± 4 | 159 ± 4 |
| 1 | 170 ± 4 | 171 ± 5 |
| 2 | 162 ± 6 | 168 ± 6 |
| 3 | 174 ± 6 | 171 ± 6 |
| 4 | 170 ± 7 | 174 ± 9 |
| 5 | 161 ± 9 | 168 ± 7 |
| 6 | 175 ± 6 | 169 ± 6 |
| 7 | 171 ± 5 | 170 ± 9 |
| 8 | 173 ± 5 | 172 ± 6 |
| 9 | 170 ± 5 | 169 ± 7 |

The number of patients with a decrease in ALT by 30% or more from the baseline in groups.

TABLE 9

| Group | Total number of patients in the group | The number of patients in the group with a decrease in ALT by 30% or more |
|---|---|---|
| Control | 9 | 1 |
| Patients taking derivative No. 1 | 30 | 23 |

The number of patients with a decrease in ASAT by 30% or more from the baseline by groups.

TABLE 10

| Group | Total number of patients in the group | The number of patients in the group with a decrease in ASAT by 30% or more |
|---|---|---|
| Control | 9 | 1 |
| Patients taking derivative No. 1 | 30 | 23 |

The number of patients with a decrease in gamma glutaminetransferase by 30% or more from the baseline by groups.

TABLE 11

| Group | Total number of patients in the group | The number of patients in the group with a decrease in GGTP by 30% or more |
|---|---|---|
| Control | 9 | 2 |
| Patients taking derivative No. 1 | 30 | 25 |

The number of patients with a decrease in ALT by 30% or more from the baseline by groups.

TABLE 12

| Group | Total number of patients in the group | The number of patients in the group with a decrease in ALT by 30% or more |
|---|---|---|
| Control | 10 | 1 |
| Patients taking derivative No. 2 | 30 | 17 |

The number of patients with a decrease in ASAT by 30% or more from the baseline by groups.

TABLE 13

| Group | Total number of patients in the group | The number of patients in the group with a decrease in ASAT by 30% or more |
|---|---|---|
| Control | 10 | 1 |
| Patients taking derivative No. 2 | 30 | 19 |

The number of patients with a decrease in gamma glutaminetransferase by 30% or more from the baseline by groups.

TABLE 14

| Group | Total number of patients in the group | The number of patients in the group with a decrease in GGTP by 30% or more |
|---|---|---|
| Control | 10 | 2 |
| Patients taking derivative No. 2 | 30 | 25 |

Morphometric indices of the experimental animals treated with derivative No. 4 of the combined toxic liver damage caused by dichloroethane and phenacetin (day 10 of the experiment)

TABLE 15

| | Experimental groups | | | |
|---|---|---|---|---|
| Indices | Intact animals | Without treatment | Enteral administration of derivative No. 4 | Parenteral administration of derivative No. 4 |
| Body weight, g | 190 ± 5 | 150 ± 10 | 180 ± 15 | 185 ± 5 |

Biochemical indices of the experimental animals treated with derivative No. 4 of the combined toxic liver damage caused by dichloroethane and phenacetin (day 10 of the experiment)

TABLE 16

| | Experimental groups | | | |
|---|---|---|---|---|
| Indices | Intact animals | Without treatment | Enteral administration of derivative No. 4 | Parenteral administration of derivative No. 4 |
| 1 | 2 | 3 | 4 | 5 |
| Total protein, g/l | 64 ± 2 | 28 ± 4 | 52 ± 5 | 48 ± 4 |
| Total lipids, g/l | 3.7 ± 0.3 | 2.9 ± 0.1 | 3.2 ± 0.1 | 2.9 ± 0.2 |
| Glucose, mmol/l | 5.0 ± 0.3 | 3.2 ± 0.4 | 4.5 ± 0.4 | 4.6 ± 0.2 |
| Cholesterol, mmol/l | 1.72 ± 0.44 | 1.92 ± 0.24 | 1.58 ± 0.21 | 1.70 ± 0.26 |
| Total bilirubin, mmol/l | 3.0 ± 0.3 | 8.2 ± 0.2 | 3.2 ± 0.1 | 3.8 ± 0.2 |
| ALT, µkat/l | 0.20 ± 0.03 | 2.55 ± 0.25 | 0.54 ± 0.08 | 0.69 ± 0.06 |
| ASAT, µkat/l | 0.60 ± 0.05 | 1.54 ± 0.17 | 0.72 ± 0.06 | 0.76 ± 0.08 |
| ALP, µkat/l | 0.69 ± 0.10 | 3.15 ± 0.35 | 0.73 ± 0.09 | 0.82 ± 0.12 |
| LDH, mmol/h/l | 4.92 ± 0.32 | 15.56 ± 1.3 | 6.82 ± 0.34 | 8.24 ± 0.35 |
| Timole test, units of turbidity | 1.46 ± 0.04 | 10.27 ± 1.5 | 2.86 ± 0.44 | 3.22 ± 0.53 |
| -SH-group, µmol/100 ml | 1650 ± 90 | 330 ± 30 | 900 ± 50 | 640 ± 50 |
| Ceruloplasmin, mg/l | 420 ± 10 | 920 ± 70 | 520 ± 50 | 580 ± 80 |
| ChE, µmol/g/min | 2.5 ± 0.1 | 1.8 ± 0.3 | 2.1 ± 0.2 | 2.2 ± 0.2 |
| Prothrombin time, s | 33 ± 5 | 92 ± 17 | 43 ± 5 | 526 ± 8 |
| Bromsulfalein, at the 10th minute after the introduction, mg % | 13.8 ± 1.2 | 54.2 ± 2.6 | 19.3 ± 1.1 | 23.0 ± 1.6 |

Liver values of the experimental animals treated with derivative No. 4 of the combined toxic liver damage caused by dichloroethane and phenacetin (day 10 of the experiment)

TABLE 17

| | Experimental groups | | | |
|---|---|---|---|---|
| Indices | Intact animals | Without treatment | Enteral administration of derivative No. 4 | Parenteral administration of derivative No. 4 |
| Reduced glutathione, mg % | 160 ± 5 | 50 ± 10 | 165 ± 10 | 170 ± 10 |
| Glycogen, mg % | 2500 ± 100 | 400 ± 60 | 1600 ± 100 | 1500 ± 200 |
| Cytochrome $P_{450}$ mmol/mg protein $\times 10^{-4}$ | 1.24 ± 0.03 | 0.72 ± 0.06 | 0.98 ± 0.06 | 1.12 ± 0.03 |
| Cytochrome $B_5$ mmol/mg protein $\times 10^{-4}$ | 0.85 ± 0.04 | 0.34 ± 0.06 | 0.54 ± 0.07 | 0.68 ± 0.04 |
| Hexenalum sleep, min | 25.0 ± 1.5 | 52.5 ± 2.5 | 27.0 ± 1.5 | 29.5 ± 1.5 |

| Preparation | Survivability by the 10th day (%) |
|---|---|
| Untreated control | 10 |
| No. 1 | 40 |
| No. 2 | 40 |
| No. 4 | 40 |
| Prototype | 30 |
| No. 1 and Prototype | 100 |
| Essentiale | 20 |
| No. 2 and Essentiale | 100 |
| Ursodeoxycholic acid | 20 |
| No. 4 and ursodeoxycholic acid | 100 |
| Substance under the patent of the Russian Federation No. 2400233* | 20 |
| No. 1 and Substance under the patent of the Russian Federation No. 2400233 | 100 |

*Derivatives of bis(2-thio-4,6-dioxo-1,2,3,4,5,6-hexahydropyrimidin-5-yl)arylmethanes.

The invention claimed is:

1. A compound 3-(4-bromophenyl)-6,6-dihydroxy-5-hydroxyiminohexahydro-2,4-pyrimidinedione and salts thereof, having a structure according to general formula:

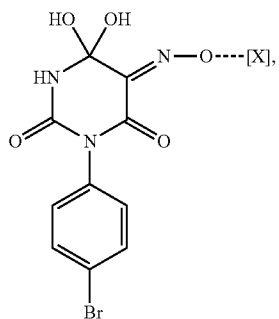

wherein X is selected from the group consisting of H, Na, K, and a hydroxyalkylammonium derivative of general formula:

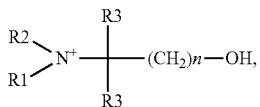

wherein R1 and R2 are selected from H, $CH_3$, $CH_2CH_3$, and $CH_2CH_2OH$; R3 is selected from H, $CH_2OH$, and n=1 or 2.

2. The compound of claim 1, wherein the compound is substantially isolated.

3. The compound of claim 1, wherein X is H and the compound is produced by reacting an aqueous solution of 1-(4-bromophenyl)violuric acid with sulfuric acid, cooling the resulting solution, and isolating the resultant solid residue.

4. The compound of claim 1, wherein X is H.

5. The compound of claim 1, wherein X is Na.

6. The compound of claim 1, wherein X is K.

7. The compound of claim 1, wherein X is

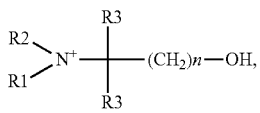

R1 and R2 are each H, R3 is $CH_2OH$, and n=1.

8. A pharmaceutical composition comprising the compound of claim 1 and a pharmaceutically acceptable carrier or excipient.

9. The pharmaceutical composition of claim 8, further comprising an additional agent selected from Heptral, Essentiale, and ursodeoxycholic acid.

10. A pharmaceutical dosage form comprising the compound of claim 1, wherein the dosage form is selected from a tablet, a capsule, a liquid, a lyophilized substrate, a suppository, a cachet, and a sweet.

11. A pharmaceutical dosage form comprising the compound of claim 1, wherein the dosage form is for enteral administration.

12. A pharmaceutical dosage form comprising the compound of claim 1, wherein the dosage form is for parenteral administration.

13. A method of treating a liver disease in a subject in need of such treatment, comprising administering to the subject a therapeutically effective amount of the pharmaceutical composition of claim 8.

14. The method of claim 13, wherein the liver disease is selected from hepatitis, intrahepatic cholestasis, hepatic encephalopathy, toxic liver damage, alcoholic liver disease, fatty hepatosis, and liver cirrhosis.

15. The method of claim 14, wherein the hepatitis is chronic hepatitis, toxic hepatitis, or alcoholic hepatitis.

16. The method of claim 13, wherein the pharmaceutical composition is administered enterally.

17. The method of claim 13, wherein the pharmaceutical composition is administered parenterally.

18. The method of claim 13, wherein the method further comprises administering an additional agent selected from Heptral, Essentiale, and ursodeoxycholic acid.

19. A method of treating a liver disease in a subject in need of such treatment, comprising administering to the subject a therapeutically effective amount of the compound of claim 1.

20. The method of claim 19, wherein the liver disease is selected from hepatitis, intrahepatic cholestasis, hepatic encephalopathy, toxic liver damage, alcoholic liver disease, fatty hepatosis, and liver cirrhosis.

21. The method of claim 20, wherein the hepatitis is chronic hepatitis, toxic hepatitis, or alcoholic hepatitis.

22. The method of claim 19, wherein the compound is administered enterally.

23. The method of claim 19, wherein the compound is administered parenterally.

24. The method of claim 19, wherein the method further comprises administering an additional agent selected from Heptral, Essentiale, and ursodeoxycholic acid.

* * * * *